United States Patent
Huang et al.

(10) Patent No.: US 9,918,944 B2
(45) Date of Patent: Mar. 20, 2018

(54) COMPOSITIONS AND METHODS FOR FORMING PROTECTIVE OR THERAPEUTIC SKIN MEMBRANES

(71) Applicant: Genepharm Biotech Corp, New Taipei (TW)

(72) Inventors: Xinfan Huang, Menlo Park, CA (US); Guan-Wei He, New Taipei (TW)

( * ) Notice: Subject to any disclaimer, the term of this patent is extended or adjusted under 35 U.S.C. 154(b) by 0 days.

(21) Appl. No.: 14/876,529

(22) Filed: Oct. 6, 2015

(65) Prior Publication Data

US 2016/0228382 A1      Aug. 11, 2016

(30) Foreign Application Priority Data

Feb. 9, 2015   (TW) .............................. 104104253 A

(51) Int. Cl.
| | | |
|---|---|---|
| A61K 9/70 | (2006.01) | |
| A61K 8/81 | (2006.01) | |
| A61K 9/06 | (2006.01) | |
| A61K 8/04 | (2006.01) | |
| A61K 47/32 | (2006.01) | |
| A61Q 17/00 | (2006.01) | |
| A61K 9/00 | (2006.01) | |
| A61K 8/34 | (2006.01) | |

(52) U.S. Cl.
CPC ............ *A61K 9/7015* (2013.01); *A61K 8/042* (2013.01); *A61K 8/34* (2013.01); *A61K 8/8152* (2013.01); *A61K 8/8158* (2013.01); *A61K 8/8176* (2013.01); *A61K 9/0014* (2013.01); *A61K 9/06* (2013.01); *A61K 47/32* (2013.01); *A61Q 17/00* (2013.01); *A61K 2800/262* (2013.01); *A61K 2800/594* (2013.01)

(58) Field of Classification Search
CPC ........ A61K 9/7015; A61K 8/042; A61K 8/34; A61K 8/8152; A61K 8/8158; A61K 9/0014; A61K 9/06; A61K 47/32; A61Q 17/00
See application file for complete search history.

(56) References Cited

U.S. PATENT DOCUMENTS 6,211,250 B1    4/2001   Tomlinson et al.

FOREIGN PATENT DOCUMENTS

| CN | 103153277 | * | 6/2013 |
|---|---|---|---|
| CN | 103153277 A | | 6/2013 |

* cited by examiner

*Primary Examiner* — Sahar Javanmard
(74) *Attorney, Agent, or Firm* — Hamre, Schumann, Mueller & Larson, P.C.

(57) ABSTRACT

A method of forming a membrane on a patch of skin using a gel, for the purpose of protecting the skin area or administering pharmacologically active substances to or through the skin area. The main ingredients of the gel are an alkyl acrylate crosspolymer such as Carbopol Ultrez 20 and a water soluble polymer such as polyvinylpyrrolidone (PVP). The gel may also contain other ingredients such as water, ethanol, antioxidants, lubricants, and neutralizers. The gel has the properties of being colorless and clear, low skin and nose irritability, easy to administer, fast membrane forming time, and removable by washing with water.

24 Claims, 6 Drawing Sheets

| # | 1st MFA | | | 2nd MFA | | Ethanol | Compositions (% w/w) | Additive | | | M.F. Time (sec) | Properties | | |
|---|---|---|---|---|---|---|---|---|---|---|---|---|---|---|
| | Ultr. | 971 | ETD | PVP | Fix. | | water | Lubr. | Antioxid. | Neutr. | | Mem. Feel | Clarity | Viscosity |
| 1 | 1.5 | | | 2.5 | | 75 | 19.45 | 0.1 | 0.1 | 1.35 | 58 | good | clear | good |
| 2 | 1.5 | | | 1.5 | | 40 | 55.45 | 0.1 | 0.1 | 1.35 | 90 | proper | clear | good |
| 3 | 1.5 | | | 1.5 | | 60 | 35.45 | 0.1 | 0.1 | 1.35 | 70 | proper | clear | proper |
| 4 | 1.5 | | | 1.5 | | 75 | 20.45 | 0.1 | 0.1 | 1.35 | 59 | proper | clear | good |
| 5 | 1.5 | | | 2 | | 60 | 34.95 | 0.1 | 0.1 | 1.35 | 70 | proper | clear | good |
| 6 | 1.5 | | | 2.5 | | 40 | 54.45 | 0.1 | 0.1 | 1.35 | 81 | good | clear | good |
| 7 | 1.5 | | | 2.5 | | 60 | 34.45 | 0.1 | 0.1 | 1.35 | 68 | good | clear | good |
| 8 | 2 | | | 1.5 | | 40 | 54.5 | 0.1 | 0.1 | 1.8 | 93 | good | clear | proper |
| 9 | 2 | | | 1.5 | | 75 | 19.5 | 0.1 | 0.1 | 1.8 | 61 | good | clear | proper |
| 10 | 2 | | | 2 | | 60 | 34 | 0.1 | 0.1 | 1.8 | 73 | good | clear | proper |
| 11 | | 1.5 | | 1.5 | | 40 | 55.45 | 0.1 | 0.1 | 1.35 | 43 | proper | gray | proper |
| 12 | | 1.5 | | 1.5 | | 60 | 35.45 | 0.1 | 0.1 | 1.35 | 35 | proper | gray | good |
| 13 | | 1.5 | | 1.5 | | 75 | 20.45 | 0.1 | 0.1 | 1.35 | 36 | proper | gray | good |
| 14 | | 1.5 | | 2 | | 60 | 34.95 | 0.1 | 0.1 | 1.35 | 36 | proper | gray | good |
| 15 | | 1.5 | | 2.5 | | 40 | 54.45 | 0.1 | 0.1 | 1.35 | 38 | proper | gray | proper |
| 16 | | 1.5 | | 2.5 | | 60 | 34.45 | 0.1 | 0.1 | 1.35 | 34 | proper | gray | good |
| 17 | | 1.5 | | 2.5 | | 75 | 19.45 | 0.1 | 0.1 | 1.35 | 35 | good | gray | good |
| 18 | | 3 | | 1.5 | | 40 | 52.6 | 0.1 | 0.1 | 2.7 | 52 | good | gray | bad |
| 19 | | 3 | | 1.5 | | 75 | 17.6 | 0.1 | 0.1 | 2.7 | 38 | good | gray | proper |
| 20 | | 3 | | 2 | | 60 | 32.1 | 0.1 | 0.1 | 2.7 | 51 | good | gray | proper |
| 21 | | | 1.5 | 1.5 | | 40 | 55.45 | 0.1 | 0.1 | 1.35 | 68 | good | gray | bad |
| 22 | | | 1.5 | 1.5 | | 60 | 35.45 | 0.1 | 0.1 | 1.35 | 32 | good | clear | proper |
| 23 | | | 1.5 | 1.5 | | 75 | 20.45 | 0.1 | 0.1 | 1.35 | 31 | proper | clear | good |

Figure 1. The test results of Examples 1-23.

| # | Compositions (% w/w) | | | | | | | | | | Mem. Form. Time (sec) | Properties | | |
|---|---|---|---|---|---|---|---|---|---|---|---|---|---|---|
| | 1st MFA | | | 2nd MFA | | Ethanol | water | Additive | | | | Mem. Feel | Clarity | Viscosity |
| | Ultr. | 971 | ETD | PVP | Fix. | | | Lubr. | Antioxid. | Neutr. | | | | |
| 24 | | | 1.5 | 2.5 | | 40 | 54.45 | 0.1 | 0.1 | 1.35 | 54 | good | cloudy | bad |
| 25 | | | 1.5 | 2.5 | | 60 | 34.45 | 0.1 | 0.1 | 1.35 | 30 | good | clear | proper |
| 26 | | | 1.5 | 2.5 | | 75 | 19.45 | 0.1 | 0.1 | 1.35 | 28 | proper | clear | good |
| 27 | | | 3 | 1.5 | | 40 | 52.6 | 0.1 | 0.1 | 2.7 | 82 | good | gray | bad |
| 28 | | | 3 | 2 | | 60 | 32.1 | 0.1 | 0.1 | 2.7 | 75 | good | clear | Middle |
| 29 | 1.5 | | | | 3 | 40 | 53.95 | 0.1 | 0.1 | 1.35 | 82 | proper | clear | good |
| 30 | 1.5 | | | | 3 | 60 | 33.95 | 0.1 | 0.1 | 1.35 | 62 | proper | clear | good |
| 31 | 1.5 | | | | 3 | 75 | 18.95 | 0.1 | 0.1 | 1.35 | 51 | proper | clear | good |
| 32 | 2 | | | | 3 | 40 | 53 | 0.1 | 0.1 | 1.8 | 85 | good | clear | proper |
| 33 | 2 | | | | 3 | 60 | 33 | 0.1 | 0.1 | 1.8 | 65 | good | clear | proper |
| 34 | 2 | | | | 3 | 75 | 18 | 0.1 | 0.1 | 1.8 | 52 | good | clear | proper |
| 35 | | 1.5 | | | 2 | 60 | 34.95 | 0.1 | 0.1 | 1.35 | 62 | proper | gray | good |
| 36 | | 1.5 | | | 3 | 60 | 33.95 | 0.1 | 0.1 | 1.35 | 60 | proper | gray | good |
| 37 | | 1.5 | | | 3 | 60 | 33.95 | 0.1 | 0.1 | 1.35 | 60 | proper | gray | good |
| 38 | | 1.5 | | | 3 | 75 | 18.95 | 0.1 | 0.1 | 1.35 | 35 | proper | gray | good |
| 39 | | 3 | | | 3 | 40 | 51.1 | 0.1 | 0.1 | 2.7 | 90 | good | gray | bad |
| 40 | | 3 | | | 3 | 60 | 31.1 | 0.1 | 0.1 | 2.7 | 84 | good | gray | proper |
| 41 | | 3 | | | 3 | 75 | 16.1 | 0.1 | 0.1 | 2.7 | 51 | good | gray | proper |

Figure 2. The test results of Examples 24-41.

| # | Compositions (% w/w) | | | | | | | | | | Properties | | | |
|---|---|---|---|---|---|---|---|---|---|---|---|---|---|---|
| | 1st MFA | | 2nd MFA | | Ethanol | water | Additive | | | | M.F. Time (sec) | Mem. Feel | Clarity | Viscosity |
| | Ultr. | 971 ETD | PVP | Fix. | | | Lubr. | Antioxid. | Neutr. | | | | | |
| 1 | 0.5 | | 1.5 | | 40 | 57.35 | 0.1 | 0.1 | 0.45 | | 84 | bad | gray | good |
| 2 | 0.5 | | 1.5 | | 75 | 22.35 | 0.1 | 0.1 | 0.45 | | 52 | bad | gray | good |
| 3 | 0.5 | | 2 | | 60 | 36.85 | 0.1 | 0.1 | 0.45 | | 67 | bad | gray | good |
| 4 | 1.5 | | 0.5 | | 40 | 56.45 | 0.1 | 0.1 | 1.35 | | 97 | bad | clear | good |
| 5 | 1.5 | | 0.5 | | 60 | 36.45 | 0.1 | 0.1 | 1.35 | | 71 | bad | clear | good |
| 6 | 1.5 | | 0.5 | | 75 | 21.45 | 0.1 | 0.1 | 1.35 | | 64 | bad | clear | good |
| 7 | | 0.5 | 1.5 | | 40 | 57.35 | 0.1 | 0.1 | 0.45 | | 37 | bad | gray | proper |
| 8 | | 0.5 | 1.5 | | 75 | 22.35 | 0.1 | 0.1 | 0.45 | | 26 | bad | gray | good |
| 9 | | 0.5 | 2 | | 60 | 36.85 | 0.1 | 0.1 | 0.45 | | 32 | bad | gray | good |
| 10 | | 1.5 | 0.5 | | 60 | 36.45 | 0.1 | 0.1 | 1.35 | | 37 | bad | gray | good |
| 11 | 0.5 | | | 3 | 40 | 55.85 | 0.1 | 0.1 | 0.45 | | 78 | bad | gray | good |
| 12 | 0.5 | | | 3 | 60 | 35.85 | 0.1 | 0.1 | 0.45 | | 60 | bad | gray | good |
| 13 | 0.5 | | | 3 | 75 | 20.85 | 0.1 | 0.1 | 0.45 | | 49 | bad | gray | good |
| 14 | 1.5 | | | 1 | 40 | 55.95 | 0.1 | 0.1 | 1.35 | | 63 | bad | clear | good |
| 15 | 1.5 | | | 1 | 60 | 35.95 | 0.1 | 0.1 | 1.35 | | 50 | bad | clear | good |
| 16 | 1.5 | | | 1 | 75 | 20.95 | 0.1 | 0.1 | 1.35 | | 46 | bad | clear | good |
| 17 | | 0.5 | | 3 | 40 | 55.85 | 0.1 | 0.1 | 0.45 | | 68 | bad | gray | proper |
| 18 | | 0.5 | | 3 | 60 | 35.85 | 0.1 | 0.1 | 0.45 | | 40 | bad | gray | good |
| 19 | | 0.5 | | 3 | 75 | 20.85 | 0.1 | 0.1 | 0.45 | | 33 | bad | gray | good |
| 20 | | 1.5 | | 1 | 40 | 55.95 | 0.1 | 0.1 | 1.35 | | 74 | bad | gray | proper |
| 21 | | 1.5 | | 1 | 60 | 35.95 | 0.1 | 0.1 | 1.35 | | 65 | bad | gray | good |
| 22 | | 1.5 | | 1 | 75 | 20.95 | 0.1 | 0.1 | 1.35 | | 58 | bad | gray | good |

Figure 3. Test results of Control 1-22, based on component variations of Example 1 in Figure 1.

| # | Composition (% w/w) | | | | Property | | | |
|---|---|---|---|---|---|---|---|---|
| | Hydroxypropyl cellulose | Acrylate/ octylpropenamide | Ethanol | Water | M.F. Time (sec) | Mem. Feel | Clarity | Viscosity |
| 23 | 3 | 1 | 66 | 30 | 80 | bad | opaque | bad |
| 24 | 1.5 | 3 | 65.5 | 30 | 44 | bad | opaque | good |

Figure 4. Test results of Control 23-24, which are prior art compositions.

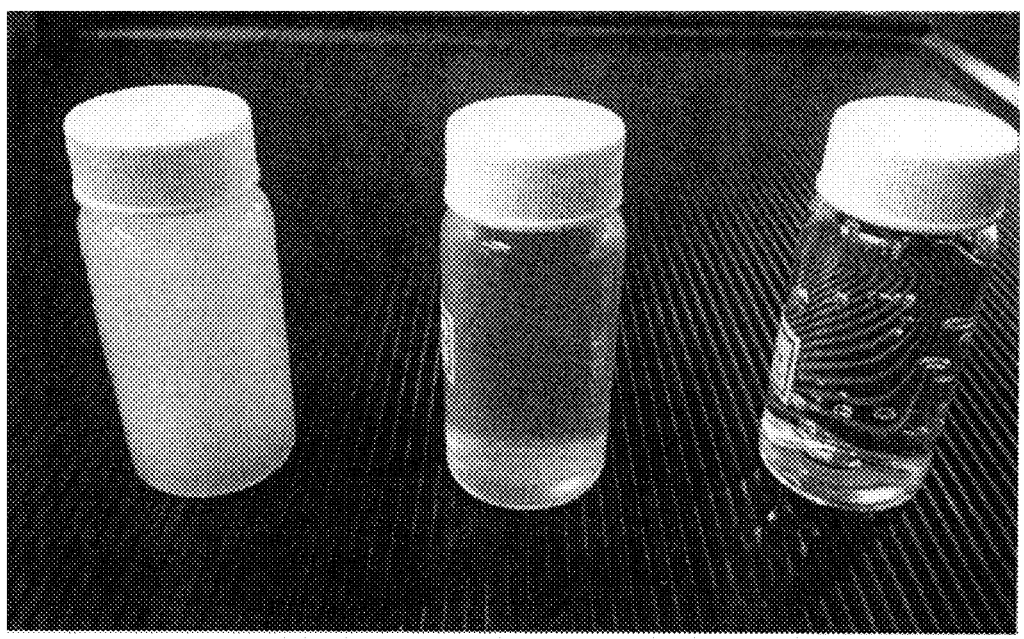
Figure 5. The membrane-forming gel products generated from Example 1 (right) and 17 (center), as well as a prior art gel, Control 23 (left). The three products also represent three different levels of gel clarity: clear (right), gray (center), and opaque (left).

| Gel Sample | Gel (mg) | Film (mg) | Film Residue after Wash (mg) | %Residue |
|---|---|---|---|---|
| Example 10 | 20 | 5.8 | 3.2 | 55.2 |
| Example 20 | 20 | 4.8 | 2.2 | 45.8 |
| Example 28 | 20 | 5.5 | 1.9 | 34.5 |
| Example 33 | 20 | 5.3 | 3.1 | 58.5 |
| Example 40 | 20 | 6.1 | 3.3 | 54.1 |
| Control 24 | 20 | 5.1 | 4.4 | 86.3 |

Figure 6. Test results showing the removability, by water washing, of the skin membrane or film formed using various different samples.

COMPOSITIONS AND METHODS FOR FORMING PROTECTIVE OR THERAPEUTIC SKIN MEMBRANES

CROSS-REFERENCE TO RELATED APPLICATIONS

Pursuant to 35 U.S.C. 119(a), this Application claims priority to patent application No. 104104253 filed in the Republic of China (Taiwan) on Feb. 9, 2015.

STATEMENT REGARDING FEDERALLY SPONSPORED RESEARCH OR DEVELOPMENT

Not Applicable

NAME OF THE PARTIES TO A JOINT RESEARCH AGREEMENT

Not Applicable

REFERENCE TO A "REQUENCE LIST", A TABLE, OR A COMPUTER PROGRAM LISTING APPENDIX SUBMITTED ON A COMPUTER DISC (CD) AND AN INCORPORATION-BY-REFERENCE OF THE MATERIAL ON THE COMPUTER DISC

Not Applicable

STATEMENT REGARDING PRIOR DISCLOSURE BY AN INVENTOR OR JOINED INVENTOR

Not Applicable

BACKGROUND OF INVENTION

This invention is related to compositions and methods for forming a thin membrane on a patch of human or animal skin for protecting the skin area or for applying therapeutic agents through the skin area.

The related prior art in this area is the so-called percutaneous delivery systems for pharmaceutically active substances ("PAS"). For example, U.S. Pat. No. 6,211,250 B1 describes a percutaneous delivery system which is a gel that contains 0.001-50% hydrophilic polymers (such as hydroxypropyl cellulose) and 0.001-50% hydrophobic polymers (such as acrylate/octylpropenamide copolymer). The gel can be applied to skin to form a film-like structure. This kind of percutaneous delivery system, though more resistant to accidental removal than traditional creams, does not form a solid membrane, and thus can still be rubbed off accidentally, preventing long-term and consistent delivery. The present inventions are compositions and methods for forming a skin membrane for the purposes of protecting the skin and/or administering PAS to or through the skin.

BRIEF SUMMARY OF THE INVENTION

The present invention includes a composition for a gel that can be used to form a membrane on a patch of skin for protecting the skin or applying PAS to or through the skin. The present invention also includes a method for using a gel to form a membrane on a patch of skin to protect the skin patch or apply PAS to or through the skin patch.

In one aspect of the invention, the membrane-forming gel comprises a first membrane-forming agent ("MFA") that is an alkyl acrylate crosspolymer (Carbopol), a second MFA that is a co-polymer formed using polyvinylpyrrolidone ("PVP") combined with 2-amino-2-methyl-1-propanol methacrylate ("AMP acrylate") and allyl methacrylate ("AMA"), and an organic solvent that is volatile and non-toxic, such as ethanol. For the purpose of administering PAS to or through a patch of skin, PAS are also added to the gel mixture.

The preferred embodiment of the present invention also includes an antioxidant and a neutralizer. The membrane-forming gel of the preferred embodiment is clear in appearance and forms the membrane in one minute or less after being administered onto the skin. The gel of the preferred embodiment also has the property of being easily removable after the desired length of time by washing with water.

In one particular embodiment of the present invention, the first MFA is one of the following three commercial products: Carbopol Ultrez 20, Carbopol 971P NF and Carbopol ETD2020.

In another particular embodiment of the present invention, the second MFA is one of the following two commercial products: PVP K90 and Fixate G-100.

In yet another particular embodiment of the present invention, the membrane forming gel contains by weight 1.5-3% of the first MFA, 1.5-3% of the second MFA, and 40-75% percent of ethanol.

BRIEF DESCRIPTION OF FIGURES

FIG. 1 is a table showing the testing results for 23 example samples embodying the present invention (the "Examples").

FIG. 2 is a continuing table from FIG. 1, showing the test results for Examples 24~41.

FIG. 3 is table testing 22 control samples which are variations of Example 1 in FIG. 1, which are referred to as Control 1~22.

FIG. 4 is a table showing as the test results in two control samples using prior art gel compositions, which are referred to as Control 23 and 24.

FIG. 5 shows three gel products. The bottle on the right contains the membrane-forming gel produced using Example 1 in FIG. 1; the bottle in the middle is Example 17 in FIG. 1; and the bottle on the left is a prior art gel produced using Control 23. The figure also illustrates the three levels of gel clarity: clear (right), gray (middle), and opaque (left).

FIG. 6 shows the removability by water wash of various samples.

DETAILED DESCRIPTION OF THE INVENTION

The membrane-forming gel of the present invention preferably has the following desired properties: (1) substantially clear, which means substant colorless and transparent; (2) forming a membrane relatively quickly after being applied onto a patch of skin; and (3) easily removable after desired time by washing with water. Such properties may be achieved by the following preferred gel components in weight: 1.5-3% of a first MFA, 1.5-3% of a second MFA, 40-75% ethanol or other suitable organic solvent, and additive substances which makes the total weight to 100%. The gel thus formed contains 90-97% in weight of the combination of water, ethanol and the additives.

The first MFA is a type of alkyl acrylate crosspolymer, such as Carbopol Ultrez 20 (Heng Hsin Co., Ltd.), Carbopol 971P NF and Carbopol ETD2020 (Top Rhyme International Co., Ltd.).

The second MFA is a water-soluble polymer, such as polyvinylpyrrolidone (PVP) or the copolymer of 2-amino-2-methyl-1-propanol methacrylate (AMP acrylate) and allyl methacrylate (AMA). An example of commercially-available PVP suitable for this purpose is PVP K90 by the First Chemical Co., Ltd. An example of the AMP acrylate/AMA copolymer is Fixate G-100 by Top Rhyme International Co., Ltd.

The portion of the MFAs used in the gel product is of significance. On one hand, if too little MFAs are used, the membrane formed will have less than desired "membrane feel," which means the solidity and evenness of the cover formed by the gel that has a "feel" of being a membrane. The membrane feel is important for this invention. A properly-portioned gel will form a thin film that solidifies to become a membrane, which will prevent accidental loss of the film due to rubbing or other physical contact. This solid and even film that resembles a membrane is referred to as "membrane" in this patent. This technique allows the PAS to be administrated onto the patch of skin covered by the membrane for a significantly longer period of time compared with the prior art gels. Thus, sufficient amount of the first and second MFAs should be used for the present inventions. On the other hand, if too many MFAs are used, the gel tends to become too thick which reduces the ease of application of the gel, especially for hairy skin areas. To balance the membrane property and thickness, the preferred portions of the two MFAs should each be 1.5-3% by weight.

The proportion of ethanol is also of significance. Ethanol functions as a solvent for the first and second MFAs. As ethanol evaporates more quickly than water, it shortens the time for the membrane formation. Thus, the more ethanol is used, the shorter the film-forming time. However, too much ethanol causes irritation to the skin, and also gives the gel a pungent smell that may be problematic for commercialization of the product. Thus, preferably, the amount of ethanol should be 40~75% by weight of the gel mixture to achieve an optimal balance between the membrane-forming time and irritation to skin and nose.

Water is an essential component of the membrane-forming gel. The main purpose of water in the additive agent is to serve as a solvent. Water can be mixed with ethanol to dissolve the two MFAs. If the combined amount of water and ethanol is over 97% by weight, it will leave too little room for the two MFAs and will reduce the product's membrane feel. Conversely, if the combined proportion of water and ethanol is lower than 90% by weight, the membrane feel of the gel will be stronger but it will be too viscous for smooth application as described above. The preferred combined proportion of water and ethanol is around 90~97% by weight.

Other additives of the membrane-forming gel may include antioxidant, neutralizer and lubricant. The lubricant lowers the friction and increases the smoothness in the gel's administration. The preferred proportion for the lubricant is 0.1% by weight. The antioxidant prevents the membrane-forming gel from degradation and spoilage and thus increases its shelf life. The preferred ratio for the antioxidant is 0.1% by weight. The neutralizer enhances the stability of the gel by increasing its pH value and viscosity. The preferred portion of the neutralizer is 90% (w/w) of the first MFA.

The primary advantage of the present invention is to use the gel with proper proportions of the first and second MFAs to form a membrane after the gel is administered onto the skin, so that the administration area is well protected and, when PAS are mixed in with the gel, to achieve long-term and steady release of the PAS.

The second advantage of the present invention is to provide the user with a good membrane feel, that is, an even membrane without a feeling of foreign object on the skin. The even membrane with its physical property and strength also reduces accidental damage or removal. The good membrane feel may be achieved by increasing the relevant amount of the first MFA. The preferred portion of the first MFA for achieving the good membrane feel is 2-3% by weight of the gel.

The third advantage of this invention is the transparency of membrane formed using the membrane-forming gel, which is referred to as being "clear" in this patent. The preferred embodiment ensuring the transparency is to use the first MFA at 2-3% by weight. For the best effect on clearness, Carbopol Ultrez 20 and Carbopol ETD2020 should be used as the first MFA. The transparency of the film-forming gel helps the consumers determine the gel's condition and whether it is proper or safe to use by detecting its color change or cloudiness.

The fourth advantage of this invention is the short membrane-forming time. A preferred embodiment for achieving this advantage is to use 1.5% (w/w) of Carbopol Ultrez20 as the first MFA, 2.5% (w/w) of PVP K90 as the second MFA, and 75% (w/w) of ethanol. This preferred embodiment can produce membranes with good membrane feel, transparency, and a short membrane-forming time that is 1 minute or shorter. A fast membrane-forming time greatly lowers the risk of accidental loss of the gel due to physical contact before the formation of the membrane. If faster than 1 minute membrane-forming time is desired, Carbopol 971P NF may be used as the first MFA, with 1.5~2.5% (w/w) of the second MFA, which results in the membrane-forming time being only about 40 seconds. Furthermore, in the above condition, if Carbopol 971P NF is kept at 3% (w/w), in addition to fast membrane-forming time, the membrane will also have the good membrane feel as discussed above. The membrane-forming time can be further shortened to 30 seconds by using 1.5% (w/w) of Carbopol ETD2020 as the first MFA, 2.5% (w/w) of PVP K90 as the second MFA, and 60~75% (w/w) of ethanol. Therefore, besides Carbopol 971P NF, Carbopol ETD2020 can also be used as the first MFA to achieve the fast membrane-forming time.

The fifth advantage of this invention is to provide a membrane-forming gel with low skin irritability. The preferred embodiment for this advantage is to lower ethanol to 40% (w/w). Such low-irritability gel may be used on patients who have sensitive skin conditions.

The sixth advantage of this invention is to provide a membrane-forming gel that can be easily cleaned. For this advantage, the preferred embodiment is to use 2-3% (w/w) each of the first and second MFAs and 60% (w/w) of ethanol. Thus-formed membrane, though solid with even thickness, can be easily washed away with water.

FIGS. 1 and 2 show the results of testing various samples that embody the present invention (the "Examples"). For these Examples, one of the following first MFAs was used: Carbopol Ultrez 20 ("Ultr."), Carbopol 971P NF ("971"), or Carbopol ETD2020 ("ETD"). One of two second MFAs was used: PVP K90 ("PVP") or Fixate G-100 ("Fix."). Various portions of ethanol, water, lubricant ("Lubr."), antioxidant ("Antioxid."), and neutralizer ("Neutr.") were also added into the gel mixture of the Examples. The membrane-forming time ("M.F. Time") of the gel was measured by seconds. The membrane feel ("Mem. Feel") and viscosity of the gel was rated with three levels: good, proper, and bad. The transparency of the gel was rated by three levels: "clear" means transparent, "gray" means mostly or semi-transparent with visible particles, and "opaque" means cream-like opaque appearance. The gels of clear, gray, and opaque are shown in FIG. 5. The detailed testing protocols are described below.

The Evaluation of the Examples Embodying the Invention

Example 1 in FIG. 1 has the following ingredients by weight: 1.5% of Carbopol Ultrez 20, 2.5% of PVP K90, 75% of ethanol, 19.45% of water, 0.1% of the lubricant Caprylic/Capric triglyceride (purchased from Top Rhyme International Co., Ltd.), 0.1% of the antioxidant Butylated hydroxytoluene (purchased from First Chemical Co., Ltd.), and 1.35% of the neutralizer 2-Amino-2-methyl-1-propanol (purchased from Top Rhyme International Co., Ltd.). The membrane-forming gel was made by thoroughly mixing these ingredients. Then, various properties of the gel were tested, including the gel's membrane-forming time, membrane feel, clarity, and viscosity.

The test of the membrane feel and membrane-forming time were conducted by administering a thin layer of the gel to the skin surface of 32° C. temperature. The counting of the membrane-forming time started immediately upon the administration of the gel and lasted until the surface of the gel turned into a dry, non-sticky and slightly shimmering thin film on the skin surface. The membrane-forming time ("M.F. Time") for Example 1 is shown as 58 seconds in FIG. 1. The evaluation of the membrane feel is then conducted, with three levels of rating. The "bad" membrane feel meant the gel could not form membrane at all. The "proper" membrane feel indicated that, although the gel could form membrane, the membrane thickness was slightly uneven. The "good" membrane feel meant that the gel formed an even-thickness membrane. For Example 1, the membrane feel was rated "good" as shown in FIG. 1.

The viscosity of the gel was evaluated through the mixing process. A rating of "good" means the gel has low viscosity, the bubbles generated during the mixing naturally rise to the surface and disappear, and the gel has good fluidity. A viscosity rating of "proper" means the gel has intermediate viscosity to enable certain fluidity but does not allow the mixing bubbles to rise to the surface to disappear. A viscosity rating of "bad" means high viscosity to the extent that, in addition to bubbles incapable of rising to the surface, the gel does not exhibit much fluidity at all. The viscosity of Example 1 was rated as "good" as shown in FIG. 1.

Examples 2~41 in FIGS. 1 and 2 have slightly different compositions compared to Example 1, but identical testing procedures and assessment standards.

The Evaluation of Control Samples

FIG. 3 shows the testing results of samples that were used to control the effect of changing certain ingredients of Example 1. These control samples are referred to as Controls 1~22. In those samples, when either the first MFA or second MFA was reduced to less than 1.5% (w/w), the gel failed to form membrane as shown in FIG. 3.

FIG. 4 shows the testing results for Controls 23 and 24, which were based on the formulations provided in U.S. Pat. No. 6,211,250 B1. The first and second MFA of the present invention was replaced with the hydroxypropyl cellulose (a hydrophilic polymer) and acrylate/octylpropenamide copolymer (a hydrophobic polymer), respectively, as the main components of the gel. Thus-obtained gel of the prior art could not form membrane at all, as shown in FIG. 4. In contrast, in the present invention, when the first and second MFA are each 1.5~3% by weight, the gel can form the membrane irrespective of the relative portions of the MFAs or ethanol, as shown by the Examples in FIGS. 1 and 2. As discussed earlier, this membrane-forming property of the present invention enables better protection of the administering area and longer and more consistent release of the PAS through the membrane.

The prior art compositions in Controls 23 and 24 are both cream-colored opaque gel. The preferred embodiments of the present invention, in contrast, have a colorless and transparent appearance. For example, in Example 1, the gel formed using, by weight, 1.5% of Carbopol Ultrez 20, 2.5% of PVP K90, and 75% of ethanol is clear, in addition to having a short membrane-forming time (less than 1 minute) and a good membrane feel. From Examples 1~41 in FIGS. 1 and 2, it can be concluded that the use of Carbopol Ultrez 20 is the key to obtaining transparent membrane-forming gel. Examples 1~10 and 29~34 all used Carbopol Ultrez 20 as the first MFA, and they were all clear. Using Carbopol ETD2020 as the first MFA can achieve the gel clarity in some examples, while using Carbopol 971P NF as the first MFA always led to the somewhat cloudy and grayish appearance of the gel.

The tests on Examples 1~41 in FIGS. 1 and 2 also provided clues for obtaining good membrane feel. The key is to use 2% (w/w) or higher of the first MFA. Examples 8-10, 18-20, 27-28, 32-34 have 2% (w/w) or higher amount of the first MFA and are shown to have good membrane feel regardless of the types of first MFA used. In addition, when Carbopol Ultrez 20 is used at 2% (w/w) or higher, the gel is also transparent as discussed above.

The tests on Examples 1~41 in FIGS. 1 and 2 also provided clues to obtaining short membrane-forming time. Although Examples 8 and 32 exhibit good membrane feel and gel clarity, the membrane-forming time in these samples is significantly longer than most of the other Examples. On the other hand, Examples 11~20, 22~23, 25~26 and 35~38, have shorter membrane-forming time in general. When the first MFA is Carbopol 971P NF, these Examples have membrane-forming times around one minute or less. When the second MFA of these samples is 1.5~2.5% (w/w) of PVP K90, the membrane-forming time can be further shortened to 43 seconds or less (e.g., Examples 11~17).

These Examples also show that good viscosity can be obtained in most cases when the first MFA is 1.5% (w/w) of Carbopol 971P NF. Further, the membrane-forming time may be shortened to around 30 seconds when the first MFA is 1.5% (w/w) of Carbopol ETD2020 and the second MFA is 1.5~2.5% (w/w) of PVP K90 with 60~75% (w/w) of ethanol, as shown in Examples 22~23 and 25~26, for instance.

In addition to the selection of MFAs, ethanol can also affect the membrane-forming time. While decreasing the amount of ethanol can lower the irritation level of the product, the membrane-forming time increases with the reduction of ethanol. Using Carbopol 971P NF as the first MFA can maintain the short membrane-forming time when ethanol level is reduced to minimize the irritability level of the gel, as shown in Examples 11, 15 and 18, for instance. Conversely, when a higher irritability is not a concern and thus higher ethanol level can be used, those first MFAs that promote better overall membrane properties (membrane feel, clarity and viscosity) but had relatively longer membrane-forming time should be used, such as Carbopol Ultrez20. For instance, comparing Example 2 and 4, where ethanol is increased from 40% to 75%, the membrane-forming time is decreased by at least 30 seconds, from 90 seconds to 59 seconds. Similarly, such 30-second reduction in membrane-forming time, due to increased ethanol, can also be seen between Examples 29 and 31, and between 32 and 34. When Carbopol 971P NF is used as the first MFA, a nearly 40-second reduction in the membrane-forming time is achieved by increasing ethanol from 40% to 75%, comparing Example 39 to 41. Therefore, low irritation can be achieved by using low level of ethanol, such as 40%, while fast membrane-forming time can be obtained by increasing the ethanol level to 75%.

Controls 1~22 in FIG. 3 also show that, if either the first MFA or the second MFA is lower than 1.5% by weight, the membrane feel of the gel deteriorates and the gel fails to form membrane. Moreover, even when Carbopol Ultrez 20 is used as the first MFA, the gel can still lose its clarity if the first MFA is lower than 1.5% by weight.

FIG. 5 shows the gel products from Example 1 (right), Example 17 (center), and Control 23 (left). Control 23, which is a prior art percutaneous delivery gel, cannot form membrane at all. The prior art gel also has a cream-colored, opaque appearance, as contrasted with the clear and semi-clear appearance (i.e., gray) of the membrane-forming gels of the present invention.

The Evaluation of the Ease of Removal

The ease of removal by water of the membrane formed from the gels of the present invention is tested using Examples 10, 20, 28, 33, and 40, and compared to the prior art using Control 24. The test results are shown in FIG. 6. The test is conducted by taking a sample of 20 milligrams of each gel and applying the sample on human skin surface at 32° C. . Wait for the water and ethanol to vaporize so that a thin film is formed. Then use a piece of adhesive tape to cleanly lift out the film, and measure the weight of the film, which is recorded in FIG. 6 as "Film (mg)." The same test is then repeated, except that the film is not removed by tape but by washing with water, accompanied by hand rubbing. Then use tape to lift the residue of the film and weigh the residue. The residues of the samples are listed as "Film Residue after Wash (mg)" in FIG. 6. The percentage of the residue of the film is then calculated using the formula:

% Residue=Film Residue after Wash/Film×100%.

The prior art sample, Control 24, which is composed of Acrylate/octylpropenamide, is not easy to wash off with water: nearly 90% of film remained after the wash. The examples of the invention, in contrast, have residues ranging from 35% to 59%. Thus, the present invention has the advantage of easy removal of the membrane with water. This ease of removal with water also indicates a low probability of causing adverse skin reaction to the gel of the invention, as the chance of the film blocking the pores on skin surface is significantly reduced.

The above examples and tests are merely specific embodiments of the present invention. The present invention is defined by the claims set for below, and should not be narrowed by the additional limitations described in the embodiments.

We claim:

1. A gel for forming a thin membrane on human or animal skin, comprising:
 a first membrane-forming agent that is an alkyl acrylate crosspolymer;
 a second membrane-forming agent that is a substantially water-soluble polymer; and
 an organic solvent that is volatile, nontoxic, and substantially water soluble,
 wherein said gel is capable of being spread onto a patch of the skin in a thin layer and forming a membrane shortly after the spreading,
 the second membrane-forming agent is either polyvinylpyrrolidone (PVP) or a copolymer of 2-amino-2-methyl-propyl acrylate (AMP acrylate) and allyl methacrylate (AMA), and
 the first membrane-forming agent and the second membrane-forming agent each constitute 1.5-3% by weight of the gel.

2. The gel of claim 1, further comprising a pharmacologically active substance.

3. The gel of claim 2, further comprising an antioxidant.

4. The gel of claim 3, further comprising a neutralizer.

5. The gel of claim 1, wherein the first membrane-forming agent is one of the following: Carbopol Ultrez 20, Carbopol 971P NF and Carbopol ETD2020.

6. The gel of claim 1, wherein the second membrane-forming agent is one of the following: PVP K90 and Fixate G-100.

7. The gel of claim 1, wherein the organic solvent is 40-75% percent by weight of the gel.

8. The gel of claim 1, wherein the first membrane-forming agent is one of the following: Carbopol Ultrez 20, Carbopol 971P NF and Carbopol ETD2020, the second membrane-forming agent is one of the following: PVP K90 and Fixate G-100, and the organic solvent is ethanol.

9. The gel of claim 1, wherein the gel is clear.

10. The gel of claim 1, wherein the gel forms the membrane within 1 minute after being spread onto the skin.

11. The gel of claim 1, wherein the gel is substantially free of irritability to skin and nose.

12. The gel of claim 1, wherein the membrane is substantially removable by washing with water.

13. A method for forming a thin membrane on human or animal skin for protecting a patch of skin or for cutaneous administration of a pharmacologically active substance, comprising:
 making the gel of claim 1;
 applying a thin layer of the gel onto a patch of skin; and
 waiting for a short time for the gel to form a membrane on the patch of skin.

14. The method of claim 13, wherein the ingredients further comprise a pharmacologically active substance.

15. The method of claim 13, further comprising substantially removing the membrane after a desired length of time by washing with water.

16. The method of claim 13, wherein the ingredients further comprises an antioxidant.

17. The method of claim 13, wherein the ingredients further comprises a neutralizer.

18. The method of claim 13, wherein the first membrane-forming agent is one of the following: Carbopol Ultrez 20, Carbopol 971P NF and Carbopol ETD2020.

19. The method of claim 13, wherein the second membrane-forming agent is one of the following: PVP K90 and Fixate G-100.

20. The method of claim 13, wherein the first membrane-forming agent and the second membrane-forming agent are each 1.5-3% of the gel by weight, and the organic solvent is 40-75% percent of the gel by weight.

21. The method of claim 13, wherein the first membrane-forming agent is one of the following: Carbopol Ultrez 20, Carbopol 971P NF and Carbopol ETD2020, the second membrane-forming agent is one of the following: PVP K90 and Fixate G-100, and the organic solvent is ethanol.

22. The method of claim 13, wherein the gel has the additional property of being clear.

23. The method of claim 13, wherein the gel having the additional property of forming the membrane in less than 1 minute after being spread onto the skin.

24. The method of claim 13, wherein the gel is substantially free of irritability to skin and nose.

\* \* \* \* \*